(12) United States Patent
Jun et al.

(10) Patent No.: US 6,368,618 B1
(45) Date of Patent: Apr. 9, 2002

(54) COMPOSITION AND METHOD FOR ENHANCED TRANSDERMAL ABSORPTION OF NONSTEROIDAL ANTI-INFLAMMATORY DRUGS

(75) Inventors: H. Won Jun; Lisheng Kang, both of Athens, GA (US)

(73) Assignee: The University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/346,187

(22) Filed: Jul. 1, 1999

(51) Int. Cl.$^7$ .......................... A61F 13/00; A61K 9/00; A61L 15/16

(52) U.S. Cl. ...................... 424/449; 424/400; 424/444; 514/938; 514/969; 514/871; 514/825

(58) Field of Search ............................... 424/449, 484; 514/944, 159

(56) References Cited

U.S. PATENT DOCUMENTS

| | | | |
|---|---|---|---|
| 5,093,133 A | * | 3/1992 | Wisniewski et al. ........ 424/484 |
| 5,104,656 A | | 4/1992 | Seth et al. |
| 5,210,099 A | * | 5/1993 | Mody et al. ................. 514/557 |

(List continued on next page.)

FOREIGN PATENT DOCUMENTS

| | | |
|---|---|---|
| CA | 2082310 | 5/1994 |
| EP | 0 499 399 A1 | 8/1992 |
| EP | 0 581 587 | 2/1994 |
| GB | 2 236 250 | 4/1991 |
| JP | 62033116 | 2/1987 |

(List continued on next page.)

OTHER PUBLICATIONS

Adams et al.,"Pharmacological differences between the optical isomers of ibuprofen: evidence for metabolic inversion of the (−)–isomer", *J. Pharm. Pharmacol.*, 28:256–257 (1976).

Adams et al., "The Optical Isomers of Ibuprofen", *Curr. Med. Res. Opin.*,3:552–555 (1975).

Büyüktimkin et al., "Preparation and enhancing effect of 1–(N,N–dimethylamino)–2–propanol dodecanoate (DAIPD) on the transepidermal penetration of clonidine, hydrocortisone, and indomethacin through shed snake skin", *Int. J. Pharm.*, 118:113–119 (1995).

Hatanaka et al., "Effect of vehicle on the skin permeability of drugs: polyethylene glycol 400–water and ethanol–water binary solvents", *J. Controlled Rel.*, 23:247–260 (1993).

Itoh et al., "Use of Shed Snake Skin as a Model Membrane for in vitro Percutaneous Penetration Studies: Comparison with Human Skin", *Pharm. Res.*, 7:1042–1047 (1990).

(List continued on next page.)

*Primary Examiner*—Thurman K. Page
*Assistant Examiner*—Isis Ghali
(74) *Attorney, Agent, or Firm*—Mueting, Raasch & Gebhardt, P.A.; Victoria A. Sandberg

(57) ABSTRACT

A novel topical formulation for delivery of nonsteroidal anti-inflammatory drugs (NSAIDs) is characterized by enhanced transdermal absorption and efficacy. A two phase liquid composition has aqueous and oil phases, the oil phase having a relatively high concentration of the NSAID to enhance transdermal absorption and efficacy when incorporated into the topical anti-inflammatory formulation. The two phase liquid composition preferably contains, in addition to an NSAID, at least one melting point depressing agent. A preferred topical anti-inflammatory composition includes S(+)-ibuprofen, thymol, and ethyl alcohol or isopropyl alcohol.

40 Claims, 1 Drawing Sheet

A

B

U.S. PATENT DOCUMENTS

| | | | | |
|---|---|---|---|---|
| 5,318,960 | A | * 6/1994 | Toppo | 514/159 |
| 5,430,194 | A | 7/1995 | Barner et al. | |
| 5,614,178 | A | * 3/1997 | Bloom et al. | 424/60 |
| 5,618,522 | A | * 4/1997 | Kaleta et al. | 424/60 |
| 5,725,874 | A | 3/1998 | Oda et al. | |

FOREIGN PATENT DOCUMENTS

| | | |
|---|---|---|
| JP | 1242521 | 9/1989 |
| JP | 06-199701 | 7/1994 |
| JP | 7316075 | 12/1995 |
| WO | WO 91/04733 | * 4/1991 |
| WO | WO 94/26309 | 11/1994 |
| WO | WO 95/24179 | 9/1995 |
| WO | WO 96/05834 | 2/1996 |
| WO | WO 97/30698 | 8/1997 |
| WO | WO 97/49405 | 12/1997 |
| WO | WO 98/51283 | * 11/1998 |
| WO | WO 99/09954 | 3/1999 |
| WO | WO 99/22716 | 5/1999 |
| WO | WO 97/30699 | 8/1999 |

OTHER PUBLICATIONS

Stott et al., "Transdermal delivery from eutectic systems: enhanced permeation of a model drug, ibuprofen", *J. Controlled Rel.*, 50:297–308 (1998).

Aoki et al., "Compatibility of Ibuprofen and Ethenzamide," *Drug Dev. Ind. Pharm.*, 23(6):561–565 (1997).

Burger et al., "RS–Ibuprofen and S–Ibuprofen (Dexibuprofen)—Binary System and Unusual Solubility Behaviour," *Eur. J. Pharm. Biopharm.*, 42(2):142–147 (1996).

Dwivedi et al., "Ibuprofen racemate and enantiomers: Phase diagram, solubility and thermodynamic studies," *Int. J. Pharm.*, 87(1–3):95–104 (1992).

Goto, "Studies on Development of Pharmaceutical Preparation with the Purpose of Improving Controlled–Release and Bioavailability," *Yakugaku Zasshi* (*Journal of the Pharmaceutical Society of Japan*), 115(11):871–891 (1995) (In Japanese; English abstract included).

Kleinbloesem et al., "Pharmacokinetics and Bioavailability of Percutaneous Ibuprofen," *Arzneimittel Forschung/Drug Research*, 45(10):1117–1121 (1995).

Lee et al., "Effect of Hydrophilic and Lipophilic Vehicles on Skin Permeation of Tegafur, Alclofenac and Ibu profen with or without Permeation Enhancers," *Biol. Pharm. Bull.*, 16(12):1264–1269 (1993).

Romero, "Optimization of ibuprofen formulation: Molecular pharmaceutics of the biologically active stereoisomer," Dissertation submitted in partial fulfillment of the requirements fo the degree of doctor of philosophy in pharmaceutical sciences, University of Rhode Island, 292 pages (1991).

Romero et al., "Efforts de formulation du stérèoisomére thérapeutique de l'ibuprofène (Efforts toward the formulation of the therapeutic stereoisomer of ibuprofen)," *J. Pharm. Belg.*, 48(1):27–32 (1993) (In French; English abstract included).

Romero et al., "Stereochemical Aspects of the Molecular Pharmaceutics of Ibuprofen," *J. Pharm. Pharmacol.*, 45(4):258–262 (1993).

Stolt et al., "Eutectic Formulations of Ibuprofen to Enhance Transdermal Permeation," Abstract P2.066, Third European Congress of Pharmaceutical Sciences, Edinburgh, Scotland, Sep. 15–17, *Eur. J. Pharm. Sciences*, 4(Suppl):S147 (1996).

Millership et al., "Topical Administration of Racemic Ibuprofen," *Chirality*, 9(3):313–316 (1997).

Swinyard, "Local Anesthetics", *Remington's Pharmaceutical Sciences*, Chapter 55, pp. 986 and 988 (1975).

* cited by examiner

COMPOSITION AND METHOD FOR ENHANCED TRANSDERMAL ABSORPTION OF NONSTEROIDAL ANTI-INFLAMMATORY DRUGS

BACKGROUND OF THE INVENTION

Rheumatoid arthritis and related conditions are some of the most prevalent diseases throughout the world. In the U.S., over 30 million patients suffer from these debilitating diseases which are characterized by painful and swollen joints due to inflammation in the musculoskeletal tissues of the joints. Over the course of the disease, thickening of the synovial membranes and deformity of the afflicted joints can develop. Although etiology of the disease is unknown, changes in autoimmune functions in genetically susceptible individuals have been often implicated as the primary cause of the disease.

For many decades, non-steroidal anti-inflammatory drugs (NSAIDs) have played an important role in treating these diseases. Among the many NSAIDs which have been introduced, ibuprofen has become one of the most widely used due to its proven efficacy and low cost. Ibuprofen is highly effective for the treatment of many types of inflammatory and arthritic diseases such as rheumatoid arthritis, arthralgia, tendinitis, gout, ankylosing spondylitis, and other related conditions. Due to its potent analgesic and antipyretic activities, ibuprofen is also effective for relief of pain and fever, and is commonly used to relieve muscle ache, neuralgia, dysmenorrhea, headache, and fever.

Oral administration of many NSAIDs, including ibuprofen, can cause serious adverse effects such as gastrointestinal bleeding and ulceration, liver and kidney damages, and central nervous system and cutaneous disturbances, particularly after extended use. Therefore, in an effort to minimize the adverse effects associated with oral administration, non-oral delivery of NSAIDs has been extensively investigated in recent years. Transdermal delivery, in particular, is an attractive option because it avoids the hepatic first-pass metabolism, reduces the side effects associated with oral administration, is associated with higher patient compliance and, in some cases, enhances therapeutic efficacy of the drug.

Although topical administration of certain NSAIDs, such as naproxen, ketoprofen, diclofenac, piroxicam and ibuprofen has been shown to deliver the drug to the local musculoskeletal tissues of joints where arthritic conditions often develop, there is much need to improve efficacy of topically applied NSAIDs. The effectiveness of topical administration of many NSAIDs is limited by the inability of these drugs to permeate the skin. The lack of clinical activity of topical NSAIDs in the treatment of rheumatoid diseases has been attributed to insufficient permeation of the drug through the stratum corneum, the major barrier of the skin towards entry of foreign chemicals. Indeed, among the many factors that potentially affect drug permeation across the skin from topical/transdermal formulations, diffusion of the drug from the vehicle toward the skin surface and subsequent partitioning into the stratum corneum are of particular importance. Some of the approaches that have been used to improve the dermal permeation of drugs are to increase lipophilicity of the drug, to incorporate the drug into lipid vesicles such as liposomes and to employ a permeation enhancer in the formulation. Despite the clear advantages of topical/transdermal therapy as opposed to systemic therapy, the absence of effective transdermal formulations of NSAIDs in the marketplace indicates that efforts directed toward improving the delivery system are extremely important for these drugs.

In most conventional topical formulations of NSAIDs that are commercially available, the active ingredients are simply dissolved, dispersed or otherwise formulated in a suitable pharmaceutical vehicle. The thermodynamic activity of the drug in such formulations is relatively low due to the limited solubility of drugs in the vehicle. For example, in the conventional pharmaceutical creams which are often used as a vehicle for topical delivery, the drug is first dissolved in an oil and then emulsified. For example, in U.S. Pat. No. 5,318,960 (Toppo, issued Jun. 7, 1994) it was disclosed that an ibuprofen-containing composition was formulated by admixing an oil surfactant with an amount of the drug, then adding alcohol and water to obtain an oily dispersion that can be further formulated for improved transdermal delivery. However, the use of a quantity of oil to dissolve the drug dilutes drug concentration in the topical preparation and thus reduces the thermodynamic activity of the active ingredient in the vehicle, the primary driving force for percutaneous absorption. In addition, the limited amount of drug that is dissolved in the oil phase has to diffuse through the surrounding inert oil layer in order to reach the skin surface prior to absorption. Diffusion through the inert oil can be the rate-limiting step in the partitioning of drugs to the skin.

Moreover, some conventional topical formulations containing high amounts of ibuprofen and long chain polymers as solubilizers are unstable, as ibuprofen can react with long chain polymers and has a tendency to crystallize on storage. In an effort to improve the stability of topical pharmaceutical compositions containing ibuprofen, WO 91/04733 (Smith et al.) discloses a eutectic mixture (oily melt) of ibuprofen and menthol, which is formulated into a topical gel containing 3–4%, by weight, of ibuprofen. However, depending on the relative proportion of menthol and ibuprofen, one or both may be present partially in microcrystalline form. In addition, the thermodynamic activity of ibuprofen in the oil phase is relatively low due to the presence of large amounts of menthol (up to 50%).

Stott et al. examined other eutectic systems for transdermal delivery of ibuprofen and found that a binary system consisting of 40:60 ibuprofen:thymol (w/w) showed a eutectic melting point of 32° C., which is about the same as the skin temperature used for their permeation studies (*J. Controlled Release*, 50: 297–308 (1998)). However, any composition of ibuprofen:thymol, other than the 40:60 eutectic mixture, was a two phase system with some of the component remaining as solid. Mixtures containing ibuprofen and L-menthol showed a eutectic melting point of 19° C. at 30:70 ibuprofen:L-menthol (w/w), and compositions containing ibuprofen in a ratio of 40:60 were liquid at 32° C. Similarly, mixtures containing ibuprofen and LD-menthol showed a eutectic melting point of 13° C. at 25:75 ibuprofen:LD-menthol (w/w). Thus, the only binary mixtures potentially suitable for topical formulations of ibuprofen as an oily melt were those having very narrow compositional ranges and containing relatively low amounts of ibuprofen. The permeability through human epidermal membranes was enhanced when ibuprofen was delivered by way of a eutectic formulation. The largest flux increase at 32° C. was obtained from ibuprofen:thymol mixtures at the weight ratios that included the eutectic compositions (35:65 and 40:60, w/w). Notably, increased flux was not observed for saturated ibuprofen:thymol mixtures above 40:60, w/w. On the other hand, maximum fluxes for the ibuprofen:menthol mixtures were observed for mixtures containing ibuprofen in concentrations high enough (e.g., 50:50 ibuprofen:LD-menthol, w/w) to contain some solid at 32° C., analogous to a saturated solution. The authors warn, however, that if the amount of ibuprofen is further increased, the system becomes "too solid" and difficult to apply to the membrane.

Chemically, ibuprofen is a-methyl-4-(2-methylpropyl) benzene-acetic acid. It has one chiral center, thus there are two enantiomers, S(+)-ibuprofen and R(−)-ibuprofen, also known as S-ibuprofen and R-ibuprofen. The racemic form consisting of equal amounts of S(+)-ibuprofen and R(−)-ibuprofen is exclusively used in presently available commercial preparations. Racemic ibuprofen a high melting point (about 78° C.), while both stereoisomers of ibuprofen, S(+)-ibuprofen and R(−)-ibuprofen, melt at 44° C. All these forms are poorly soluble in water. And, although ibuprofen is a lipophilic drug, it does not permeate the skin well. Notably, the S(+) form alone appears to be responsible for the anti-inflammatory activity, not the R(−) form (S. Adams et al., *Curr. Med. Res. Opin.*, 3, 552 (1975); S. Adams et al., *J. Pharm. Pharmacol.*, 28, 256–257 (1976)). Accordingly, some investigators have described anti-inflammatory compositions containing substantially pure S(+)-ibuprofen.

Japanese patent application JP 06199701 describes anti-inflammatory analgesic compositions comprising ibuprofen (up to 1%, by weight), preferentially in the S(+)-form, and a high concentration of polyhydric alcohol that purportedly increases absorption of the drug from the skin. Due to the presence of a large amount of alcohols in the formulations, the majority of NSAIDs will be dissolved in the vehicle. U.S. Pat. No. 5,093,133 (Wisniewski et al., Mar. 3, 1992) describes topical compositions containing somewhat higher concentrations of S(+)-ibuprofen, but these compositions also contain high concentrations of alcohols, as much as 50%., which solubilize ibuprofen without forming a large oil phase.

Since pharmacological actions depend on drug concentrations at pathological sites, it is readily apparent that effective transdernal delivery of clinically significant amounts of NSAIDs, especially ibuprofen, to a target site remains an important challenge for pharmaceutical scientists.

SUMMARY OF THE INVENTION

A novel composition is provided that can be readily formulated into a topical anti-inflammatory preparation. Preferred embodiments of the anti-inflammatory preparation of the invention are characterized by enhanced transdermal absorption. The composition has two liquid phases: an aqueous phase and an oil phase, wherein the oil phase has a relatively high concentration of a nonsteroidal anti-inflammatory drug (NSAID). An aqueous phase is a phase that comprises water. Preferably, both the aqueous phase and the oil phase are homogeneous. A "homogenous" aqueous phase or oil phase is a liquid phase in which none of the components is present in a solid state. The aqueous and oil phases of the composition of the invention are preferably homogenous phases at about 37° C.; more preferably, they are homogenous phases at about 25 ° C. It should nonetheless be understood that the invention also encompasses two phase liquid compositions that contain nonhomogenous aqueous and/or oil phases; that is, the presence of some crystalline solids in the aqueous phase or the oil phase, or both, is not necessarily excluded.

The concentration of the anti-inflammatory agent in the oil phase of the composition is preferably at least about 40%, by weight, of the weight of the oil phase; more preferably it is at least about 50%, by weight, of the weight of the oil phase; even more preferably it is at least about 60%, by weight, of the weight of the oil phase; most preferably it is at least about 70%, by weight, of the weight of the oil phase of the composition.

A preferred two phase liquid composition of the invention contains:

(a) at least one nonsteroidal anti-inflammatory drug (NSAID), preferably at least about 1% of the total composition, by weight, more preferably at least about 3% of the total composition, by weight, most preferably at least about 5% of the total composition, by weight; and preferably less than about 30% of the total composition, by weight, more preferably less than about 20% of the total composition, by weight, most preferably less than about 10% of the total composition, by weight;

(b) at least one first melting point depressing agent, preferably at least about 1% of the total composition, by weight, more preferably at least about 5% of the total composition, by weight, most preferably at least about 10% of the total composition, by weight; and preferably less than about 40% of the total composition, by weight, more preferably less than about 30% of the total composition, by weight, most preferably less than about 2 0% of the total composition, by weight; and (c) water to 100%.

A preferred NSAID is one that forms an oil upon melting, and preferably has a melting point of less than about 200° C., more preferably less than about 160° C., most preferably less than about 120° C. The NSAID optionally contains at least one chiral carbon atom, in which event the NSAID present in the two phase liquid composition can be either a substantially pure stereoisomer of the chiral NSAID or a mixture of stereoisomers. Where one stereoisomer of a chiral NSAID has greater efficacy than another, a preferred composition contains the more effective stereoisomer in a relative proportion of at least about 60% of the NSAID, preferably at least about 70% of the NSAID, more preferably about 80% of the NSAID, most preferably about 90% of the NSAID. A composition in which at least 90% of the NSAID is in the form of the desired stereoisomer is considered to contain a "substantially pure stereoisomer" of the chiral NSAID.

Examples of NSAIDs include ibuprofen, ketoprofen, flurbiprofen, fenoprofen, loxoprofen, suprofen, aluminoprofen, pranoprofen, piroxicam, pentazocine, aspirin, acetanilide, phenacetin, diclofenac, antipyrine, aminopyrine, phenyl salicylate, methyl salicylate, methenamine, carprofen, choline salicylate, salsalate, diflunisal, dihydroergotamine mesylate, ergotamine tartrate, indomethacin, meclofenamate, mefenamic acid, naproxen, oxyphenbutazone, phenylbutazone, sulindac and tolmetin. Ibuprofen, ketoprofen, flurbiprofen, pranoprofen, fenoprofen, naproxen, suprofen and aluminoprofen are examples of chiral NSAIDs. Preferred NSAIDs for use in a composition of the invention include ibuprofen, ketoprofen, flurbiprofen, fenoprofen and aspirin. A particularly preferred NSAID is the S-enantiomer of ibuprofen, S(+)-ibuprofen.

The first melting point depressing agent is an alcohol; preferably it is a monohydric alcohol. Preferred monohydric alcohols include isopropyl alcohol and ethyl alcohol; a preferred polyhydric alcohol is propylene glycol. One or more alcohols can be used in combination.

The water component of the composition can be pure water or an aqueous solution. An aqueous solution can be a buffer and/or can contain a solute, such as a salt.

In a preferred embodiment, the two phase liquid composition of the invention further contains at least one second melting point depressing agent, preferably in an amount of at least about 1/20 of the weight of the NSAID, more preferably at least about 1/10 of the weight of the NSAID; and preferably less than about 3/4 of the weight of the NSAID, more preferably less than about 1/4 of the weight of the NSAID. The second melting point depressing agent is preferably thymol, menthol, eucalyptol, eugenol, methyl salicylate, phenyl salicylate, capsaicin, butylated hydroxytoluene, a local anesthetic agent, an NSAID, or any combination thereof, except that in compositions containing as the active agent a substantially pure stereoisomer of a chiral NSAID, the second melting point depressing agent is not another, less active isomer of the chiral NSAID. Examples of local anesthetic agents include lidocaine, tetracaine, prilocaine, mepivacaine, etidocaine and benzocaine. The use of a second melting point depressing agent is preferred for NSAIDs having a melting point above about 50° C. For example, a composition of the invention containing the NSAID S(+)-ibuprofen, which has a melting point of about 44° C., can contain a first melting point depressing agent and water, in the appropriate amounts, to generate the oil phase, whereas compositions containing NSAIDs such as ketoprofen and flurbiprofen, which have melting points higher than 50° C., preferably include a first melting point depressing agent and a second melting point depressing agent in order to generate the highest possible amount of the drug in the oil phase.

When the NSAID is a solid at ambient temperature, preferably a crystalline solid, melting of the NSAID yields an oil. The second melting point depressing agent can be a solid or an oil at ambient temperature. When the second melting point depressing agent is a solid, melting of the second melting point depressing agent yields an oil. Preferably, the NSAID and the second melting point depressing agent have melting points lower than about 200° C.; more preferably, they have melting points lower than about 160° C., most preferably lower than about 120° C.

Methods for making the two phase liquid composition of the invention are also provided. Components of the composition are mixed together in amounts effective to form a two phase liquid composition consisting of an aqueous phase and an oil phase. Preferably, the aqueous and oil phases are homogeneous below about 37° C., more preferably they are homogenous at or below about 25° C. During mixing, the solid components) undergo a solid to liquid phase transition; that is, they melt. Simple mixing of the components at ambient temperature causes at least some melting of the solid components without heating. In some embodiments of the invention, an external source of heat is applied to the mixture to more quickly achieve a full "melt." When an external source of heat is used during the preparation of the composition, the mixture is preferably maintained at a temperature of less than about 50° C.

The components of the two phase liquid composition of the invention partition between the aqueous phase and oil phase according to their individual physical and chemical properties to form an equilibrated system. For example, the NSAID can partition between the oil phase and the aqueous phase, in accordance with its relative solubility in each liquid phase.

Although the inventors do not intend to be bound by any particular theory or mechanism, it is believed that inclusion of the first and second melting point depressing agents in the mixture in accordance with the invention causes the solid component(s) to melt into the oil phase by depressing the melting point(s) of the solid component(s). More particularly, it is believed that inclusion of the first and second melting point depressing agents yields an oil phase having a higher concentration of NSAID, for example S(+)-ibuprofen, than has previously been achieved. Increasing the concentration of the NSAID in the oil phase is desirable because it enhances percutaneous absorption and efficacy. In compositions of the invention, the concentration of the NSAID in the oil phase can reach about 75% or higher, by weight, of the weight of the oil phase. This concentration has never been achieved by any previous methods. The remaining oil phase typically contains amounts of the melting point depressing agents and a trace amount of water.

The term "two phase melt system" is used herein, particularly in the Examples, to describe a two phase liquid composition of the invention that has been generated by combining the components of the composition to effect an oily "melt state" below about 37° C., preferably at or below about 25° C. It should be nonetheless understood that the composition of the invention is by no means limited to any particular method of making the composition. If no crystals remain in the oil phase and the aqueous phase of a resulting composition, it is considered that a complete melt has occurred; if crystals remain in the either the oil phase or the aqueous phase, only a partial melt has achieved. Compositions resulting from both complete or partial melts are included in the invention, although compositions resulting from complete melts are preferred.

The two phase liquid compositions of the invention are readily formulated into a cream, an emulsion, an ointment, a lotion, a lipophilic organogel, patch, or the like, that is effective in local delivery of the anti-inflammatory drug through the skin, and these pharmaceutical preparations or formulations are encompassed by the invention. A typical cream contains, by weight, at least about 0.1% NSAID, preferably at least about 0.5% NSAID, more preferably at least about 1% NSAID; and preferably less than about 30% NSAID, more preferably less than about 20% NSAID, most preferably less than about 10% NSAID. A preferred cream contains S(+)-ibuprofen as the anti-inflammatory drug, isopropyl alcohol or ethyl alcohol or both as the first melting point depressing agent, and thymol as the second melting point depressing agent. The pH of the formulation is preferably controlled such that the NSAID is supplied in a nonionized acidic form, which increases lipid solubility of the NSAID, making it more permeable through a lipid membrane.

The invention further provides a method for local transdermal delivery of an anti-inflammatory drug in animal, preferably a mammal, more preferably a human. The method employs topical application of the pharmaceutical formulation of the invention. The pharmaceutical formulation is expected to be safe and effective in delivering the anti-inflammatory drug through the skin of humans for clinical use and is suitable for use in veterinary or agricultural husbandry applications as well. The preparation can be administered to intact skin, wounded skin, or a mucus membrane of the animal. Optionally, the method includes covering the formulation with a dressing, such as a gauze, bandage, plaster, patch, or the like. The method can be performed whenever treatment of inflammation and/or pain is required or desired, such as in connection with local inflammatory and arthritic diseases such as rheumatoid arthritis, arthralgia, tendinitis, gout, and ankylosing spondylitis, and other related conditions. In a preferred embodiment, the NSAID has analgesic or antipyretic activities, or both, as well, and can be used to relieve pains associated with muscle ache, backache, neuralgia, dysmenorrhea, headache, sunburn and fever. The method preferably utilizes a pharmaceutical formulation comprising S(+)-ibuprofen due to its potent anti-inflammatory, analgesic, and antipyretic activities.

DETAILED DESCRIPTION

Figure 1:
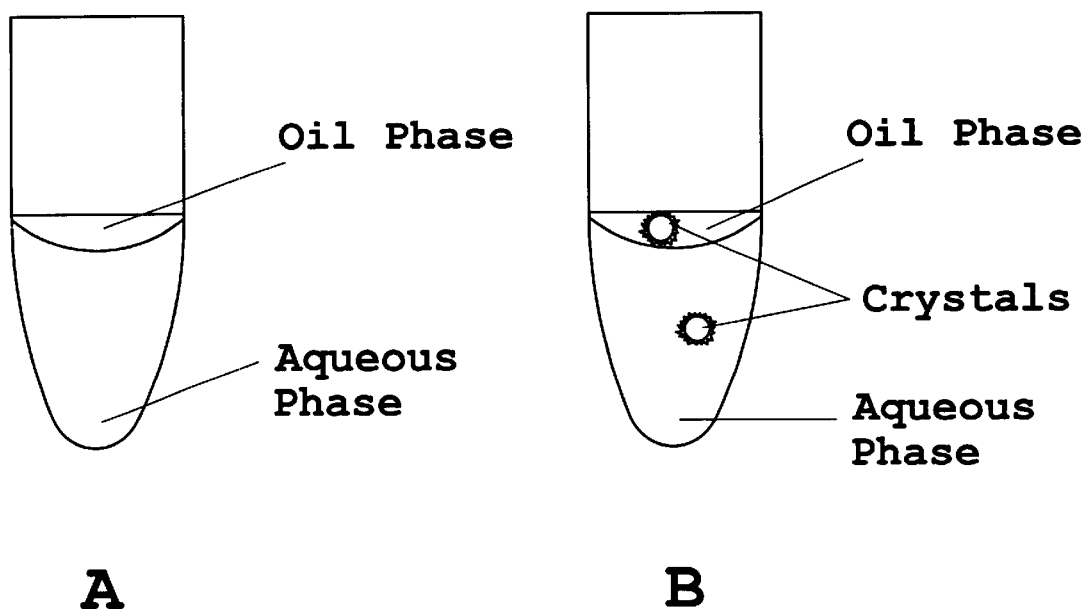
FIG. 1 illustrates (A) a two phase liquid composition having a homogenous aqueous phase and a homogenous oil phase and (B) a two phase liquid composition wherein crystals are present in the aqueous phase and the oil phase, rendering the aqueous and oil phases nonhomogeneous.

The two phase liquid composition of the invention can be made by intimately mixing an NSAID; one or more first melting point depressing agents (MP-A); one or more second melting point depressing agents (MP-B); and water within the weight ranges shown in Table 1.

TABLE 1

| NSAID | 1–30%[a] |
|---|---|
| MP-A | 1–40% |
| MP-B | 0 to 3/4 wt of NSAID |
| Water | q.s. 100 % |

[a]amounts are percentages of the total two phase liquid composition, by weight

The order in which the components are mixed is not important; they can be mixed in any order. For example, it is often convenient to first mix the solids (e.g., the NSAID and the second melting point depressing agent) then add a liquid mixture of alcohol (the first melting point depressing agent) and water.

It was discovered that isopropyl alcohol in water depresses the melting point of S(+)-ibuprofen, and a homogenous oil phase was spontaneously obtained when the isopropyl alcohol content in the composition is 15% by weight or higher (see Example I, section A).

Thymol (5-methyl-2-isopropyl-1-phenol), the preferred second melting point depressing agent, is widely used in many pharmaceutical and mouthwash products with proven safety. When S(+)-ibuprofen crystals were mixed directly with thymol crystals, some melting point depression of both S(+)-ibuprofen and thymol occurred and an oil typically formed. However, it was only possible to obtain a homogeneous oil at ambient temperature (that is, at about 20° C. to about 25° C.) with the S(+)-ibuprofen:thymol ratio between about 5:5 to 6:4 by weight (see Example I, section B). Outside this range, crystals remain in the oil phase at 25° C.; that is, the oil phase is not homogenous.

A two-phase melt system of the invention which utilizes both a first and/or a second melting point depressing agent was discovered to achieve a higher concentration of S(+)-ibuprofen in the oil phase than has previously been attainable (see Example I, sections C and D). Additionally, thymol, menthol, ethyl alcohol and isopropyl alcohol are all known as effective transdermal permeation enhancers, thus further possibly assisting the transdermal absorption of S(+)-ibuprofen in the preferred formulations.

The two-phase liquid composition of the invention can be directly formulated into a cream or other desired topical anti-inflammatory preparation using methods well-known to those of skill in the art. To form a preparation suitable for topical application to a patient, the two phase liquid composition is introduced into a pharmaceutically acceptable vehicle such as a cream, emulsion, ointment, gel, patch, plaster or the like. Optionally, the pharmaceutical formulations include one or more accessory ingredients including excipients, buffers, surface active agents, thickeners, preservatives, permeation enhancers, fragrance, coloring agents, and the like. Also optionally, the pharmaceutical formulations of the invention include antimicrobial agents, antiseptics, antioxidants, anesthetics, permeation enhancers, vitamins, and the like. Antioxidants include ascorbic acid and α-tocopherol.

The high concentration of the NSAID in the oil phase of the composition of the invention improves transdermal absorption of the active components through the skin. Local and regional pharmacological effect is obtained by topical application of the anti-inflammatory preparation on the skin surface. Preferably, the anti-inflammatory preparation is applied at a dose of about 0.1 g to about 2 g of the anti-inflammatory preparation per $cm^2$ of skin. The amount of NSAID administered per dose is preferably about 0.1 $mg/cm^2$ to about 100 $mg/cm^2$ of skin; more preferably it is about 0.3 $mg/cm^2$ to about 50 $mg/cm^2$ of skin.

In a preferred embodiment of the two phase liquid composition of the invention, the majority of the oil phase (typically over about 65%, w:w) is S(+)-ibuprofen, thus the drug is directly available for partitioning into the stratum corneum without the rate-limiting diffusion process from the inert oil phase as in a conventional cream. For S(+)-ibuprofen, as much as 76% of the oil phase is the therapeutic compound. In addition, the enhanced transdermal delivery of S(+)-ibuprofen, the active form of ibuprofen, directly to the target site increases the clinical efficacy of this drug, which possibly reduces the therapeutic dose in patients compared with the conventional topical formulations of racemic ibuprofen. Although preferred for use on intact skin, the composition can also be formulated for use on wounded skin, burned skin, or on mucous membranes.

The invention is illustrated by the following examples. However, the particular materials and amounts thereof recited in these examples, as well as other conditions and details, are to be interpreted to apply broadly in the art and should not be construed to unduly restrict or limit the invention in any way.

EXAMPLE 1

Melting Point Depression of S(+)-ibuprofen in the Presence of Thymol and Isopropyl Alcohol A. Melting Point Depression of S(+)-ibuprofen in the Presence of Aqueous Isopropyl Alcohol When S(+)-ibuprofen is dispersed in an aqueous isopropyl alcohol (IPA) solution containing 10–30% (w:w) isopropyl alcohol in water, oil droplets are spontaneously formed at ambient temperature, well below the melting point of S(+)-ibuprofen. To further investigate the relationship between the melting points of S(+)-ibuprofen and the isopropyl alcohol content in the mixture, S(+)-ibuprofen (0.5 g) was mixed with different amounts of isopropyl alcohol (0.5–2.0 g) in a pH 4.0 acetate buffer (0.02 M sodium acetate) solution at 25° C. The total weight of each mixture was 10 g. After mixing, the dispersions were stored at 25° C. and the melt states of S(+)-ibuprofen were examined weekly for 3 months using an optical microscope.

The two types of dispersions typically observed are shown in FIG. 1. FIG. 1-A represents a two phase melt system with homogeneous oil and aqueous phases, and FIG. 1-B represents a system where complete melt is not achieved. When the isopropyl alcohol contents were 10% or less by weight of the total composition, S(+)-ibuprofen did not completely melt at 25° C. (FIG. 1-B). When the isopropyl alcohol content was 15% or higher, S(+)-ibuprofen completely transformed into an oil at 25° C. (FIG. 1-A).

The composition of the oil phase formed in the dispersion containing 15% isopropyl alcohol was determined by the gas chromatography-mass spectrometry (GC-MS) analysis. The results showed that the concentration of S(+)ibuprofen was 68.4% (w:w) in the oil, indicating that the oil was a mixture of S(+)-ibuprofen, isopropyl alcohol and possibly some water.

When this test was repeated at 25° C. with the exception that racemic ibuprofen was used in place of S(+)-ibuprofen to prepare the samples as described in Table 2, complete melt was never achieved even if the isopropyl alcohol content was 25% or higher, by weight, of the total composition, probably due to the higher melting point of racemic ibuprofen (78° C.).

TABLE 2

Melt States of S(+)-ibuprofen[a] in Aqueous Isopropyl Alcohol (IPA) at 25° C.

|  | 5% IPA | 10% IPA | 15% IPA | 20% IPA |
|---|---|---|---|---|
| 25° C. | S | S | O | O |

[a]5% S(+)-ibuprofen (by weight, relative to the total composition)
S—solid crystals present (FIG. 1-B)
O—no crystals present (FIG. 1-A)

B. Melting Point Depression of S(+)-ibuprofen in the Presence of Thymol

The melting points of S(+)-ibuprofen (SI) and thymol (T) are 44° C. and 52° C., respectively. To investigate the physicochemical interaction and melting properties of these two compounds in various physical mixtures, S(+)-ibuprofen (Albemarle Corporation, Baton Rouge, La.) and thymol (Sigma Chemical Company, St. Louis, Mo.) in the SI:T ratios from 1:9 to 9:1 (w:w) were intimately mixed in a glass test tube and stored at 25° C. The melt states of the two compounds were then examined weekly for 3 months using an optical microscope. It was found that the physical mixtures within the SI:T ratios of 5:5 to 6:4 (w:w) spontaneously formed a homogeneous oil at ambient temperature (20–25° C.). Outside this range, however, an oil and some crystals of the compounds co-existed in the mixture, indicating that complete melting of the compounds did not occur.

C. Melting Point Depression of S(+)-ibuprofen in the Presence of Thymol and Aqueous Isopropyl Alcohol Since thymol and isopropyl alcohol can individually depress the melting point of S(+)-ibuprofen, the effects of the two compounds in combination on the melting point of S(+)-ibuprofen were studied. A 3-factor factorial design as shown in Table 3 was used to examine the melting states of S(+)-ibuprofen in the presence of thymol and aqueous isopropyl alcohol simultaneously at three different temperatures, 25, 15 and 4° C. Since thymol alone is capable of depressing the melting point of S(+)-ibuprofen to below 25° C. within the SI:T ratios of 5:5–6:4 (w:w), only the SI:T ratios higher than the upper range (>6:4) were included in the study.

Crystalline S(+)-ibuprofen (0.5 g) was mixed with 0.125, 0.088 or 0.056 g of thymol and 1.0, 1.5, 2.0 or 2.5 g of isopropyl alcohol in pH 4.0 acetate buffer (0.02 M sodium acetate) at 25° C. (10 g total weight). Replicate samples of these mixtures were prepared at 25° C. and were stored at 25, 15, and 4° C. for three months. During storage, the melt states of the composition were examined weekly using an optical microscope. The results are shown in Table 3, where O and S denote systems described as in FIG. 1-A and 1-B, respectively, at the corresponding temperature. Clearly, there is a predictive relationship among the SI:T ratios, the isopropyl alcohol contents and the melt states of S(+)-ibuprofen in the mixture. The lower the SI:T ratio and the higher the alcohol content, the lower the melting range of the solid components in the mixture, as shown by the attainment of the melt state. Comparing these results as well as the effect of thymol alone on the melting point of S(+)-ibuprofen (as described in Example 1-A) with the data shown in Table 2, it is clear that a more significant melting point depression effect was observed when both thymol and aqueous isopropyl alcohol were present in the mixture, rather than only one of them present. Thus the use of thymol and aqueous isopropyl alcohol in combination allows the preparation of two phase melt systems with the highest possible SI:T ratio and the lowest isopropyl alcohol content at 25° C.

TABLE 3

Melt States of S(+)-ibuprofen (SI) and Thymol (T) in Aqueous Isopropyl Alcohol (IPA)

| SI:T[a] | ° C. | 10%[a] IPA | 15% IPA | 20% IPA |
|---|---|---|---|---|
| 90:10 | 25 | S | O[I] | O[III] |
|  | 15 | S | O | O |
|  | 4 | S | O | O |
| 85:15 | 25 | O | O[II] | O[IV] |
|  | 15 | S | O | O |
|  | 4 | S | O | O |
| 80:20 | 25 | O | O | O |
|  | 15 | O | O | O |
|  | 4 | O | O | O |

[a]by weight
S—solid crystals present
O—no solid crystals present

When this test was repeated at 25° C. with the exception that racemic ibuprofen was used as the substitute for S(+)-ibuprofen to prepare the samples as described in Table 3, complete melt of the solids was never achieved.

D. S(+)-ibuprofen Concentrations in the Oil Phase of the Equilibrated Two Phase Melt System After ultracentrifugation at 20,000 rpm for 30 minutes at 25° C. of selected two phase melt systems (Systems I, II, III and IV as shown in Table 3) that had been stored at 25° C. for three months, a portion of the oil phase of these melt systems was removed using a micro-sampling tube and was weighed accurately by a taring method. After extraction with methylene chloride, the samples were analyzed by GC-MS to determine the concentrations of S(+)-ibuprofen and thymol in the oil phase. The results are shown in Table 4.

TABLE 4

Composition of Oil Phase in the Select Two-phase Melt Systems

| Melt Systems | % SI[b] | % T[b] | % Residual[d] |
|---|---|---|---|
| I[a] | 76.3 ± 5.4[c] | 10.1 ± 0.7 | 13.4 ± 5.8 |
| II[a] | 67.3 ± 4.9 | 14.8 ± 0.3 | 17.9 ± 4.5 |
| III[a] | 54.1 ± 1.7 | 20.4 ± 13.7 | 25.5 ± 15.3 |
| IV[a] | 51.6 ± 10.2 | 12.3 ± 1.63 | 5.8 ± 12.1 |

[a]Compositions of the select Melt Systems shown in Table 3
[b]% SI or T = amount (g) of SI or T detected in 100 g of the oil phase.
[c]Mean ± SD (n = 3)
[d]Residual = 100 − (% SI + % T)

The concentrations of S(+)-ibuprofen in the oil phases of the melt systems analyzed by GC-MS were consistently higher than 50% (w:w) and reached as high as 76% (w:w). These high concentrations of S(+)-ibuprofen in an oil have not been achieved by any previously known methods. The sum of SI and T in the oil phase is less than 100%, due to the presence of isopropyl alcohol and possibly a trace amount of water. It is found that, for a given concentration of isopropyl alcohol, the higher the initial SI:T ratio used, the higher the S(+)-ibuprofen concentration in the oil phase formed.

Generation of a homogenous oil phase containing a high concentration of S(+)-ibuprofen, as in the selected two phase melt systems shown in Table 3, thus depends upon the relative amounts of the therapeutic agent, the first melting point depressing agent, MP-A, and the second melting point depressing agent, MP-B, in the two phase melt systems. A preferred two phase melt system is characterized by a high possible SI:T ratio and a low amount of isopropyl alcohol. The low alcohol content may contribute to the long-term physical stability of the cream, emulsion, or other delivery system prepared.

EXAMPLE 2

S(+)-ibuprofen 0.5 g, isopropyl alcohol 1.5 g, LD-menthol 0.088 g (Sigma Chemical Company, St. Louis, Mo.) and pH 4.0 acetate buffer (0.02 M sodium acetate) 7.9 g were intimately mixed at 25° C. in a glass test tube. The two phase melt system that was spontaneously formed can be readily formulated into creams, emulsions, organogels, patches, and the like for topical/transdermal application.

EXAMPLE 3

Example 2 was repeated with the exception that the menthol was substituted by an equal weight of methyl salicylate. The two phase melt system that was spontaneously formed can be readily formulated into creams, emulsions, organogels, patches, and the like for topical/transdermal application.

EXAMPLE 4

Example 2 was repeated with the exception that the menthol was substituted by an equal weight of phenyl salicylate. The two phase melt system that was spontaneously formed can be readily formulated into creams, emulsions, organogels, patches, and the like for topicall-transdermal application.

EXAMPLE 5

Example 2 was repeated with the exception that the menthol was substituted by an equal weight of eucalyptol (1,8-epoxy-p-methane). The two phase melt system that was spontaneously formed can be readily formulated into creams, emulsions, organogels, patches, and the like for topical/transdermal application.

EXAMPLE 6

Example 2 was repeated with the exception that the menthol was substituted by an equal weight of lidocaine (2-diethylamino-N-2,6-dimethylphenylacetamide). The two phase melt system that was spontaneously formed can be readily formulated into creams, emulsions, organogels, patches, and the like for topical/transdermal application.

EXAMPLE 7

Example 2 was repeated with the exception that the menthol was substituted by an equal weight of tetracaine (2-dimethylaminoethyl-4-n-butylaminobenzoate). The two phase melt system that was spontaneously formed can be readily formulated into creams, emulsions, organogels, patches, and the like for topical/transdermal application.

EXAMPLE 8

Example 2 was repeated with the exception that the menthol was substituted by an equal weight of eugenol (4-allyl-2-methoxyphenol). The two phase melt system that was spontaneously formed can be readily formulated into creams, emulsions, organogels, patches, and the like for topical/transdermal application.

EXAMPLE 9

Example 2 was repeated with the exception that the menthol was substituted by an equal weight of capsaicin (N-4-hydroxy-3-methoxybenzyl-8-methylnon-trans-6-eneamide). The two phase melt system that was spontaneously formed can be readily formulated into creams, emulsions, organogels, patches, and the like for topical/transdermal application.

EXAMPLE 10

Example 2 was repeated with the exception that the menthol was substituted by an equal weight of butylated hydroxytoluene. The two phase melt system that was spontaneously formed can be readily formulated into creams, emulsions, organogels, patches, and the like for topical/transdermal application.

EXAMPLE 11

Example 2 was repeated with the exception that the isopropyl alcohol was substituted by an equal weight of ethyl alcohol. The two phase melt system that was spontaneously formed can be readily formulated into creams, emulsions, organogels, patches, and the like for topical/transdermal application.

EXAMPLE 12

Example 2 was repeated with the exception that the isopropyl alcohol was substituted by a combination of isopropyl alcohol 1 g and ethyl alcohol 0.5 g. The two phase melt system that was spontaneously formed can be readily formulated into creams, emulsions, organogels, patches, and the like for topical/transdermal application.

EXAMPLE 13

Example 2 was repeated with the exception that the isopropyl alcohol was substituted by an equal weight of propylene glycol. The two phase melt system that was spontaneously formed can be readily formulated into creams, emulsions, organogels, patches, and the like for topical/transdermal application.

EXAMPLE 14

Example 2 was repeated with the exception that the isopropyl alcohol was substituted by a combination of isopropyl alcohol 1 g and propylene glycol 0.5 g. The two phase melt system that was spontaneously formed can be readily formulated into creams, emulsions, organogels, patches, and the like for topical/transdermal application.

EXAMPLE 15

Example 2 was repeated with the exception that the S(+)-ibuprofen was substituted by an equal weight of R(−)- ibuprofen (Chirex, Inc., Boston Mass.). The two phase melt system that was spontaneously formed can be readily formulated into creams, emulsions, organogels, patches, and the like for topical/transdermal application.

EXAMPLE 16

S-ketoprofen 0.5 g, thymol 0.3 g, isopropyl alcohol 2.0 g, and acetate buffer (0.02 M sodium acetate) 7.2 g were intimately mixed in a glass test tube at 25° C. The two phase melt system that was spontaneously formed can be readily formulated into creams, emulsions, organogels, patches, and the like for topical/transdermal application.

EXAMPLE 17

Example 16 was repeated with the exception that the S-ketoprofen was replaced by an equal weight of S-flurbiprofen. The two phase melt system that was spontaneously formed can be readily formulated into creams, emulsions, organogels, patches, and the like for topical/transdermal application.

EXAMPLE 18

Racemic ibuprofen 0.5 g, thymol 0.375 g, isopropyl alcohol 2.0 g and acetate buffer (0.02 M sodium acetate) 7.2 g were intimately mixed at 25° C. in a glass test tube. The two phase melt system that was spontaneously formed can be readily formulated into creams, emulsions, organogels, patches, and the like for topical/transdermal application.

EXAMPLE 19

Example 18 was repeated with the exception that the racemic ibuprofen was replaced by an equal weight of racemic ketoprofen. The two phase melt system that was spontaneously formed can be readily formulated into creams, emulsions, organogels, patches, and the like for topical/transdermal application.

EXAMPLE 20

Example 18 was repeated with the exception that the racemic ibuprofen was replaced by an equal weight of racemic flurbiprofen. The two phase melt system that was spontaneously formed can be readily formulated into creams, emulsions, organogels, patches, and the like for topical/transdermal application.

EXAMPLE 21

Preparation of S(+)-ibuprofen Cream

Table 5 represents a typical composition of a topical S(+)-ibuprofen cream incorporating compositions described in the previous examples.

TABLE 5

Composition of a Topical 5% S(+)-Ibuprofen Cream Prepared From the Two Phase Melt System

| | |
|---|---|
| S(+)-ibuprofen | 5%[a] |
| Thymol | 0.55% |
| Isopropyl Alcohol | 15% |
| Pemulen | 1% |
| Surfactants | 1% |
| Water | q.s. 100% |

[a]% by weight

Pemulen was obtained from B. F. Goodrich, Cleveland Ohio. After the pH was adjusted to 4.0 with phosphoric acid, the composition as shown in Table 5 was emulsified using a mechanical homogenizer. The advantage of this method is that the two phase melt systems consisting of an oil phase and an aqueous phase can be directly formulated into a therapeutic cream with the addition of selected thickening agent(s) and surfactant(s).

EXAMPLE 22

In Vitro Permeation Study of S(+)—and Racemic Ibuprofen Through Shed Snake Skin From Topical Formulations A. Preparation of Topical Formulations The permeation rate of the S(+)-ibuprofen (SI) from a 5% SI cream, and the permeation rates of racemic ibuprofen (Rac-I) from a 5% racemic ibuprofen (Rac-I) cream and from a saturated Rac-I solution, were determined using shed snake skin as a model membrane in Franz diffusion cells.

The 5% S(+)-ibuprofen cream was prepared as described in Example 21. The 5% conventional Rac-I cream was prepared by dissolving 5 g of racemic ibuprofen in 25 g of a pharmaceutical oil (Tween 85), and then emulsifying the oil with 1 g of Pemulen, 15 g of isopropyl alcohol, and 54 g of water. The pH of the cream was adjusted to 4.0 using phosphoric acid. The saturated ibuprofen solution was prepared by adding excess amount of racemic ibuprofen to an aqueous solution containing 15% isopropyl alcohol by weight, and then mildly shaking at 25° C. for 48 hours. The pH of the solution was adjusted to 4.0 with phosphoric acid.

B. Preparation of the Sample Skin

The use of shed snake skin in in vitro drug permeability studies has been widely reported and has been shown to be a good model membrane of animal origin (T. Itoh, et al., Pharm Res., 7: 1042–1047, 1990; S. Buyuktimkin, et al., Int. J. Pharm., 118: 113–119, 1995). Compared with other biological membranes such as human cadaver skin, rat skin and mouse skin, the snake skin has several advantages including easy handling and small sample variations. Prior to the study, a large piece of shed snake skin was left in distilled water for a half hour to allow complete hydration. Then the skin was cut into the proper size and was mounted on the Franz diffusion cells with the stratum corneum side contacting the donor phase.

C. Permeation Study

One gram of each of the test formulations was placed on the skin surface and the donor phase compartment was covered with a piece of PARAFILM (American National Can, Neenah, Wis.) at ambient temperature (25° C.). The receiver phase was pH 7.4 phosphate buffer that was maintained at 32° C. during the test. The effective diffusion area of the skin was 2.0 cm$^2$. Each of the three test formulations was studied with three replications. Following loading of each formulation on the skin, 0.2ml of the receptor phase was removed and replaced with blank receptor solution hourly for six hours. The drug concentrations in the samples taken were quantitated by the HPLC with UV-detection at 220 nm. The mean permeation profiles (±SD) for the three formulations tested are shown in FIG. 2.

The steady state flux ($J_{SS}$) of S(+)-ibuprofen (52.1±15.7 ug/hrcm$^2$) from the cream prepared using the two phase melt system was significantly higher than that of the racemic ibuprofen(16.5±4.6 ug/hrcm$^2$) in the conventional cream formulation (p=0.05). The $J_{SS}$ of the racemic ibuprofen from the saturated solution (28.2±11.4 ug/hrcm$^2$) was also significantly higher than that from the conventional cream (p=0.05). The addition of a large amount of a pharmaceutical oil in the conventional cream prepared apparently retarded the penetration rate of the drug probably due to the increased diffusion distance of the drug molecules through the oil phase before reaching the skin surface as well as reduced drug partitioning into the stratum corneum. Of the three delivery systems, the two phase melt system clearly provided the highest thermodynamic activity of the therapeutic agent. Without wishing to be bound by theory, it is postulated that the high permeation rate of S(+)-ibuprofen from the new cream prepared using the two phase melt system of the invention is in large part attributable to the high drug concentration in the oil phase. In addition, it is possible that the melting point of S(+)-ibuprofen in the two phase melt system was so much depressed that it became an oil, allowing increased partitioning of S(+)-ibuprofen in the lipid components of the stratum corneum. Furthermore, as mentioned earlier, S(+)-ibuprofen possesses higher pharmacological activity than R(−)-ibuprofen or a racemic mixture. It is therefore expected that the use of the new S(+)-ibuprofen cream according to the invention will provide significant improvement for the transdermal absorption and clinical efficacy of topically applied ibuprofen.

The complete disclosure of all patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A composition comprising:
    at least one nonsteroidal anti-inflammatory drug (NSAID):
    at least one alcohol selected from the group consisting of isopropyl alcohol, ethyl alcohol and propylene glycol;
    at least one melting point depressing agent selected from the group consisting of thymol, menthol, eucalyptol, eugenol, methyl salicylate, phenyl salicylate, capsaicin, butylated hydroxytoluene, a local anesthetic agent and any combination thereof, said melting point depressing agent present in the composition in an amount of less than about ¼ of the weight of the NSAID;
    said composition having spontaneously equilibrated aqueous and oil phases, wherein the NSAID is in substantially melted form at 25° C. and wherein the concentration of the NSAID in the oil phase is, by weight, at least about 40% of the weight of the oil phase.

2. The composition of claim 1 wherein the concentration of the NSAID in the oil phase is, by weight, at least about 60% of the weight of the oil phase.

3. The composition of claim 1 wherein the oil phase is homogenous at about 37° C.

4. The composition of claim 1 wherein the oil phase is homogenous at about 25° C.

5. The composition of claim 1 wherein the aqueous phase is homogenous at about 37° C.

6. The composition of claim 1 wherein the aqueous phase is homogenous at about 25° C.

7. The composition of claim 1 wherein the NSAID is a chiral NSAID present as a substantially pure stereoisomer.

8. The composition of claim 1 wherein the NSAID comprises at least one drug selected from the group consisting of ibuprofen, ketoprofen, flurbiprofen, fenoprofen, loxoprofen, suprofen, aluminoprofen, pranoprofen, piroxicam, pentazocine, aspirin, acetanilide, phenacetin, diclofenac, antipyrine, aminopyrine, phenyl salicylate, methyl salicylate, methenamine, carprofen, choline salicylate, salsalate, diflunisal, dihydroergotamine mesylate, ergotamine tartrate, indomethacin, meclofenamate, mefenamic acid, naproxen, oxyphenbutazone, phenylbutazone, sulindac and tolmetin.

9. The composition of claim 8 wherein the drug is selected from the group consisting of ibuprofen, ketoprofen, flurbiprofen, fenoprofen and aspirin.

10. The composition of claim 8 wherein the NSAID comprises a pharmacologically active stereoisomer of a drug selected from the group consisting of ibuprofen, ketoprofen, flurbiprofen, fenoprofen, suprofen, aluminoprofen, pranoprofen and naproxen.

11. The composition of claim 9 wherein the NSAID comprises ibuprofen.

12. The composition of claim 9 wherein the NSAID comprises substantially pure S(+)-ibuprofen.

13. The composition of claim 1 wherein the alcohol is isopropyl alcohol.

14. The composition of claim 1 wherein the alcohol is ethyl alcohol.

15. The composition of claim 1 wherein the NSAID comprises substantially pure S(+)-ibuprofen.

16. The composition of claim 1 wherein the melting point depressing agent comprises thymol or menthol.

17. The composition of claim 1 wherein the NSAID is about 1% to about 30% of the total composition, by weight; the alcohol is about 1% to about 40% of the total composition, by weight; and the melting point depressing agent is present in the composition in an amount of at least about 1/20 of the weight of the NSAID.

18. The composition of claim 1 wherein the NSAID is substantially pure S(+)-ibuprofen, the alcohol comprises isopropyl alcohol, and the melting point depressing agent comprises thymol.

19. A composition having spontaneously equilibrated aqueous and oil phases at 25° C., said composition comprising:
    S(+)-ibuprofen;
    at least one alcohol selected from the group consisting of isopropyl alcohol, ethyl alcohol and propylene glycol;
    at least one melting point depressing agent selected from the group consisting of thymol, menthol, eucalyptol, eugenol, methyl salicylate, phenyl salicylate, capsaicin, butylated hydroxytoluene, a local anesthetic agent and any combination thereof, said melting point depressing agent present in the composition in an amount of less than about ¼ of the weight of the S(+)-ibuprofen; and
    water; wherein the S(+) ibuprofen is present in the composition in substantially melted form at 25° C. and wherein the concentration of the S(+)-ibuprofen in the equilibrated oil phase is, by weight, at least about 40% of the weight of the oil phase.

20. A method for making a two phase liquid composition comprising:
    mixing at least one NSAID, at least one alcohol selected from the group consisting of isopropyl alcohol, ethyl alcohol and propylene glycol, at least one melting point depressing agent selected from the group consisting of thymol, menthol, eucalyptol, eugenol, methyl salicylate, phenyl salicylate, capsaicin, butylated hydroxytoluene, a local anesthetic agent and any combination thereof, wherein the amount of said melting point depressing agent is less than about ¼ of the weight of the NSAID, and water;
    to form a composition in which the NSAID is present in the composition in substantially melted form at 25° C., said composition having spontaneously equilibrated aqueous and oil phases at 25° C., said oil phase comprising at least a portion of the NSAID, wherein the concentration of the NSAID in the oil phase is, by weight, at least about 40% of the weight of the oil phase.

21. The method of claim 20 wherein the NSAID is a solid prior to mixing.

22. The method of claim 20 wherein the composition has a homogenous aqueous phase and a homogenous oil phase at about 37° C.

23. The method of claim 20 wherein the composition has a homogenous aqueous phase and a homogenous oil phase at about 25° C.

24. The method of claim 20 wherein the NSAID comprises at least one drug selected from the group consisting of ibuprofen, ketoprofen, flurbiprofen, fenoprofen, loxoprofen, suprofen, aluminoprofen, pranoprofen, piroxicam, pentazocine, aspirin, acetanilide, phenacetin, diclofenac, antipyrine, aminopyrine, phenyl salicylate, methyl salicylate, methenamine, carprofen, choline salicylate, salsalate, diflunisal, dihydroergotamine mesylate, ergotamine tartrate, indomethacin, meclofenamate, mefenamic acid, naproxen, oxyphenbutazone, phenylbutazone, sulindac and tolmetin.

25. A method for making a topical anti-inflammatory preparation comprising mixing the composition of claim 1 with at least one pharmaceutically acceptable surfactant.

26. The method of claim 25 wherein the preparation is formulated as a cream, emulsion, ointment, lotion, organogel, transdermal patch, plaster, or occlusive dressing.

27. A topical anti-inflammatory preparation comprising at least a portion of the oil phase of the composition of claim 1 and at least one pharmaceutically acceptable excipient.

28. The preparation of claim 27 further comprising at least a portion of the aqueous phase of the composition of claim 1.

29. The preparation of claim 27 formulated as a cream, emulsion, ointment, lotion, organogel, transdermal patch, plaster or occlusive dressing.

30. A topical anti-inflammatory preparation comprising at least a portion of the oil phase of the composition of claim 1 and a pharmaceutically acceptable miscible solvent.

31. The preparation of claim 30 further comprising at least a portion of the aqueous phase of the composition of claim 1.

32. The preparation of claims 27 or 30 wherein the NSAID is S(+)-ibuprofen.

33. A method for treating inflammation in an animal comprising applying the topical anti-inflammatory preparation of claims 27 or 30 to the skin or mucus membrane of the animal.

34. The method of claim 33 wherein the topical anti-inflammatory preparation is applied to the skin of the animal.

35. The method of claim 33 wherein the animal is a human.

36. The method of claim 33 wherein the NSAID has analgesic activity.

37. The method of claim 33 wherein the NSAID has antipyretic activity.

38. The method of claim 33 wherein the topical anti-inflammatory preparation is used to treat inflammation associated with rheumatoid arthritis, arthralgia, tendinitis, gout, and ankylosing spondylitis, or other related conditions, or pain associated with muscle ache, backache, neuralgia, dysmenorrhea, headache, sunburn or fever.

39. A composition made by the method comprising:

mixing at least one NSAID; at least one alcohol selected from the group consisting of isopropyl alcohol, ethyl alcohol and propylene glycol; a melting point depressing agent selected from the group consisting of thymol, menthol, eucalyptol, eugenol, methyl salicylate, phenyl salicylate, capsaicin, butylated hydroxytoluene, a local anesthetic agent and any combination thereof, wherein the amount of said melting point depressing agent is less than about ¼ of the weight of the NSAID; and water;

to cause the spontaneous formation of a composition in which the NSAID is present in substantially melted form at 25° C., said composition having equilibrated aqueous and oil phases at 25° C., said oil phase comprising at least a portion of the NSAID, wherein the concentration of the NSAID in the oil phase is, by weight, at least about 40% of the weight of the oil phase.

40. The composition of claim 39 wherein the NSAID comprises at least one drug selected from the group consisting of ibuprofen, ketoprofen, flurbiprofen, fenoprofen, loxoprofen, suprofen, aluminoprofen, pranoprofen, piroxicam, pentazocine, aspirin, acetanilide, phenacetin, diclofenac, antipyrine, aminopyrine, phenyl salicylate, methyl salicylate, methenamine, carprofen, choline salicylate, salsalate, diflunisal, dihydroergotamine mesylate, ergotamine tartrate, indomethacin, meclofenamate, mefenamic acid, naproxen, oxyphenbutazone, phenylbutazone, sulindac and tolmetin.

* * * * *